(12) United States Patent
Ginn

(10) Patent No.: US 6,702,835 B2
(45) Date of Patent: Mar. 9, 2004

(54) NEEDLE APPARATUS FOR CLOSING SEPTAL DEFECTS AND METHODS FOR USING SUCH APPARATUS

(75) Inventor: Richard S. Ginn, San Jose, CA (US)

(73) Assignee: Core Medical, Inc., Sunnyvale, CA (US)

( * ) Notice: Subject to any disclaimer, the term of this patent is extended or adjusted under 35 U.S.C. 154(b) by 22 days.

(21) Appl. No.: 09/948,453

(22) Filed: Sep. 7, 2001

(65) Prior Publication Data
US 2003/0050665 A1 Mar. 13, 2003

(51) Int. Cl.7 .................. A61B 17/08; A61B 17/06; A61B 17/00
(52) U.S. Cl. .............. 606/215; 606/216; 606/224; 606/139
(58) Field of Search ................. 606/213, 215, 606/216, 151, 224, 139; 128/898

(56) References Cited

U.S. PATENT DOCUMENTS

| 5,108,420 A | 4/1992 | Marks |
| 5,334,217 A | 8/1994 | Das |
| 5,702,421 A | 12/1997 | Schneidt |
| 5,879,366 A | 3/1999 | Shaw et al. |
| 5,908,428 A | 6/1999 | Scirica et al. |
| 5,919,200 A | 7/1999 | Stambaugh et al. |
| 5,941,899 A | 8/1999 | Granger et al. |
| 5,944,738 A | 8/1999 | Amplatz et al. |
| 6,007,563 A | 12/1999 | Nash et al. |
| 6,036,720 A | 3/2000 | Abrams et al. |
| 6,071,292 A | 6/2000 | Makower et al. |
| 6,077,281 A | 6/2000 | Das |
| 6,077,291 A | 6/2000 | Das |
| 6,080,182 A | 6/2000 | Shaw et al. |
| 6,206,907 B1 | 3/2001 | Marino et al. |
| 6,231,561 B1 | 5/2001 | Frazier et al. |
| 6,270,515 B1 | 8/2001 | Linden et al. |
| 6,290,674 B1 | 9/2001 | Roue et al. |
| 6,319,263 B1 | 11/2001 | Levinson |
| 6,458,100 B2 | 10/2002 | Roue et al. |
| 2003/0145865 A1 * | 8/2003 | Sterman et al. ............. 128/898 |

FOREIGN PATENT DOCUMENTS

| EP | 0 432 320 A1 | 6/1995 |
| WO | WO 98/02100 A1 | 1/1998 |
| WO | WO 99/02100 | 1/1999 |
| WO | WO 01/21247 | 3/2001 |

* cited by examiner

Primary Examiner—Michael J. Milano
Assistant Examiner—P Roberts
(74) Attorney, Agent, or Firm—Orrick, Herrington & Sutcliffe, LLP

(57) ABSTRACT

Apparatus and methods for closing a septal defect including a flap of tissue partially detached from a septum of a heart. A needle is advanced through a patient's vasculature within a delivery apparatus until the needle is disposed within a first chamber adjacent the septum. The needle is directed through the flap of tissue until the needle is disposed within a second chamber opposite the septum. A filament attached to an intermediate region of the needle is pulled, thereby causing the needle to pivot about the intermediate region such that the ends of the needle straddle the septal opening. A locking element is secured to the filament to secure the flap of tissue against the septum, and the filament is cut. Alternatively, the filament is biased to coil to engage the flap of tissue and secure the needle against the septum to close the opening.

11 Claims, 4 Drawing Sheets

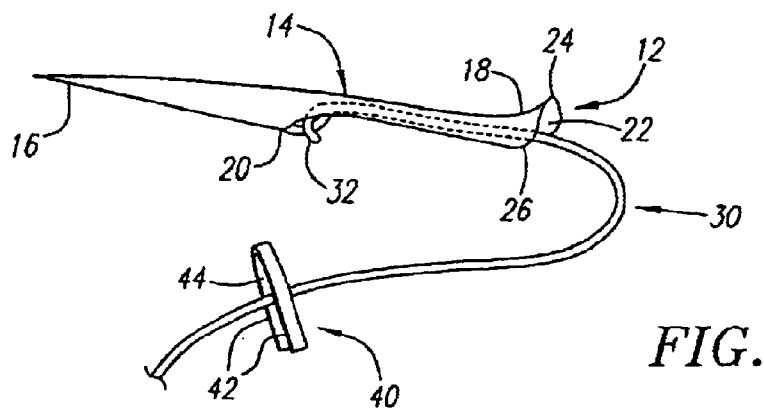
FIG. 1
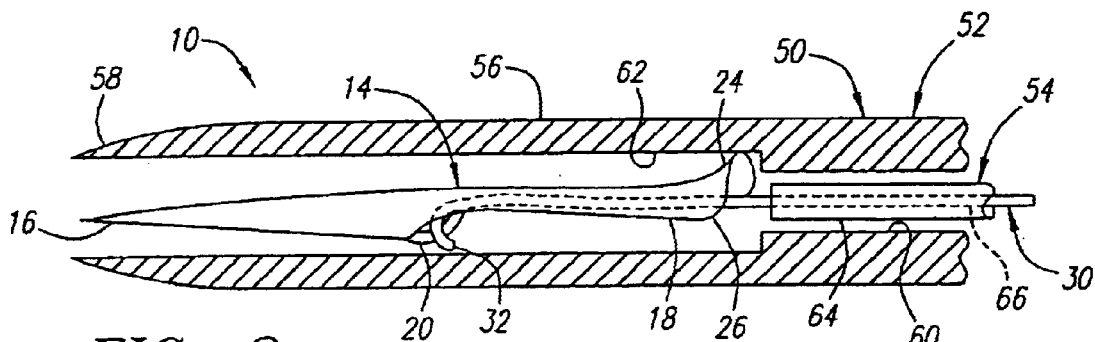
FIG. 2
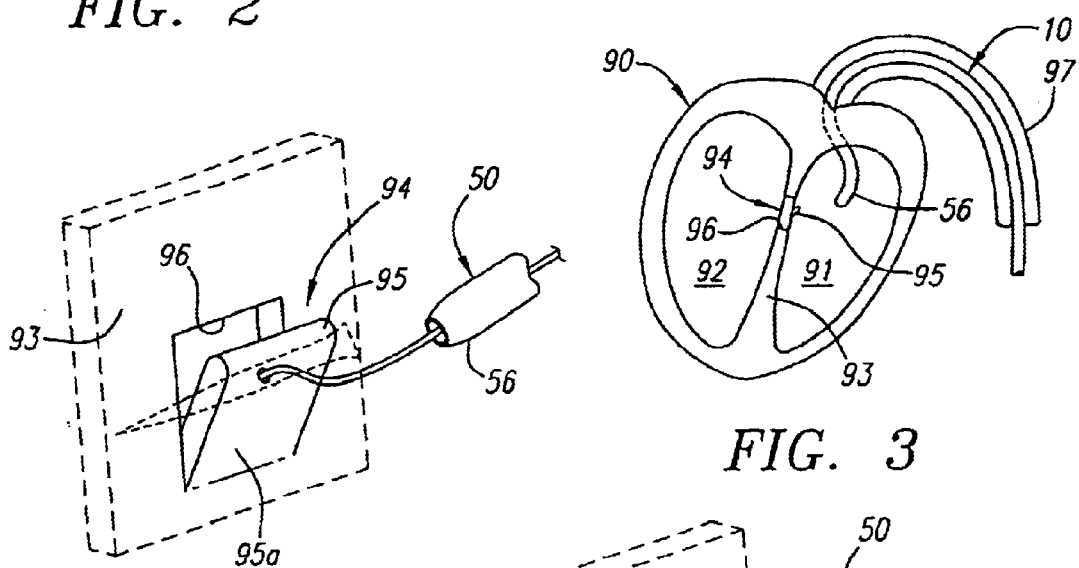
FIG. 3
FIG. 4A
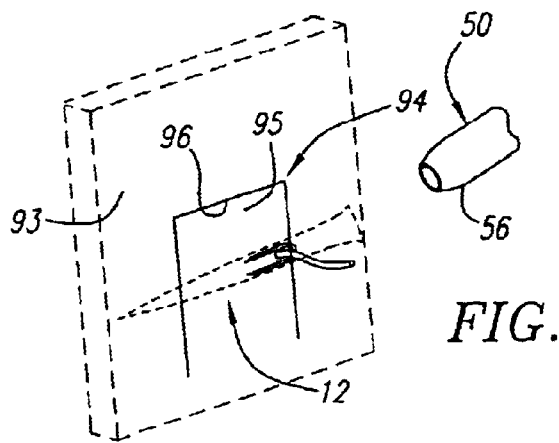
FIG. 4B

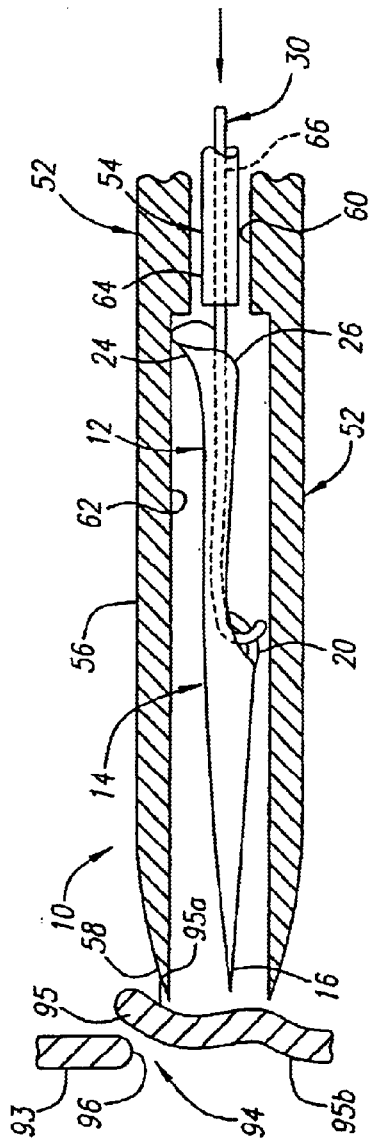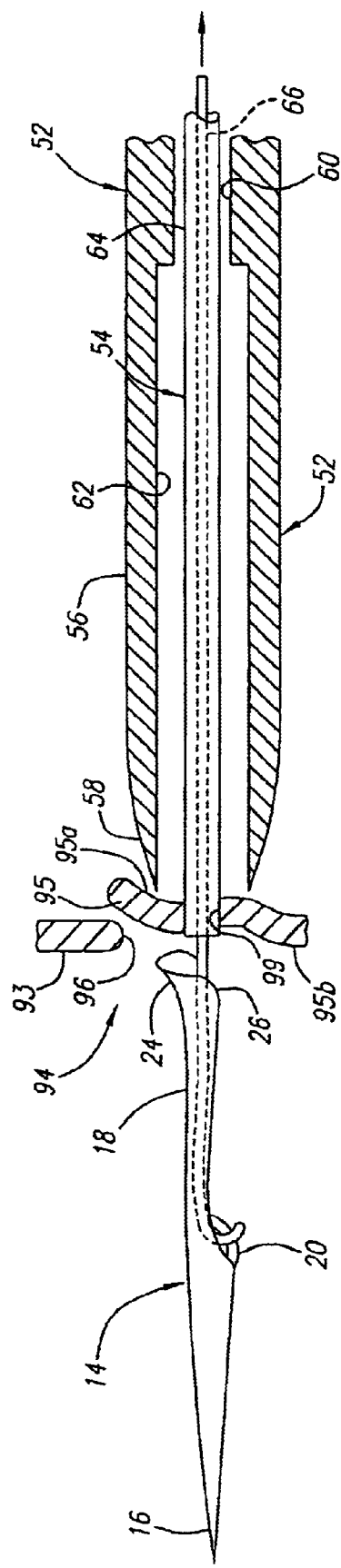

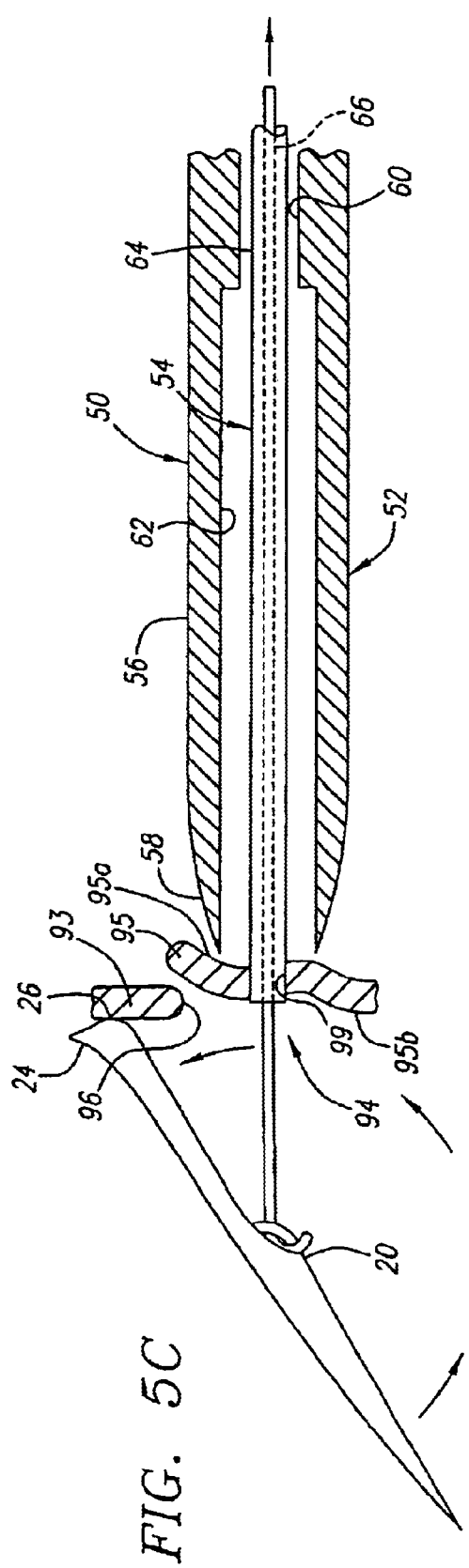
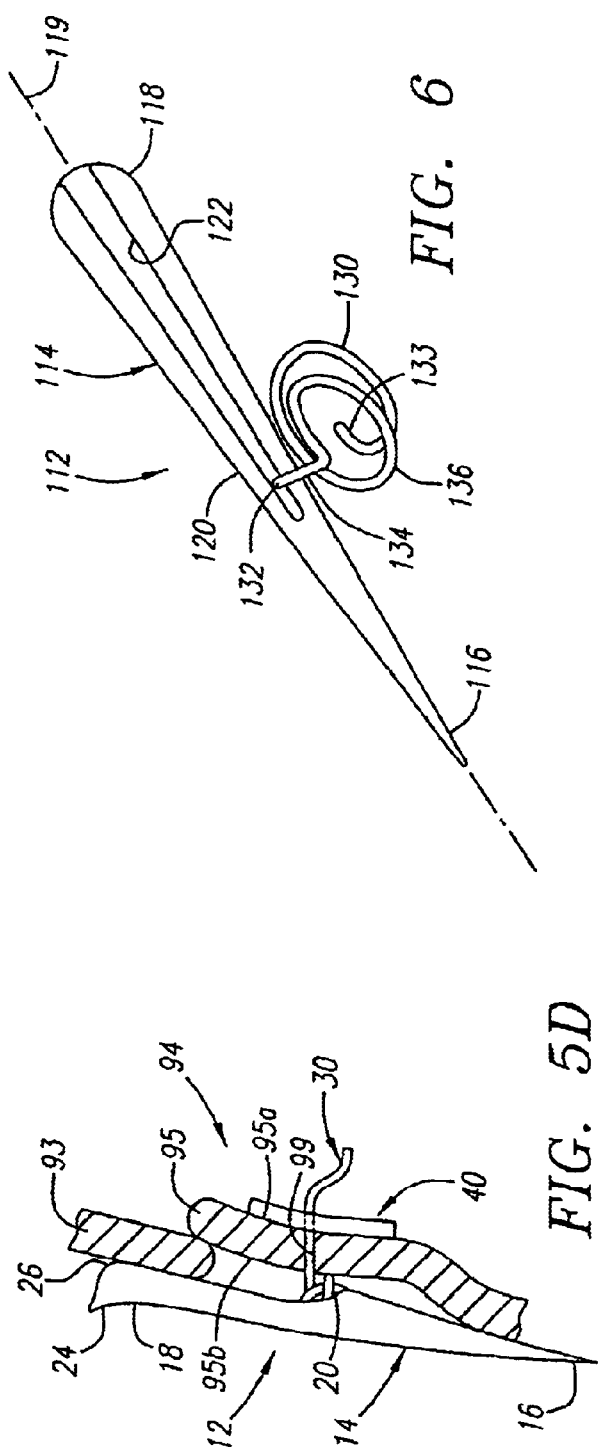

NEEDLE APPARATUS FOR CLOSING SEPTAL DEFECTS AND METHODS FOR USING SUCH APPARATUS

FIELD OF THE INVENTION

The present invention relates generally to apparatus and methods for treating septal defects, and more particularly to apparatus and methods for closing a patent foramen ovale or other septal defect that include a flap of tissue using a needle device.

BACKGROUND

During development of a fetus in utero, blood is generally oxygenated by the mother's placenta, not the fetus' developing lungs. Most of the fetus' circulation is shunted away from the lungs through specialized vessels or foramens that are open during fetal life, but generally close shortly after birth. Occasionally, however, these foramen fail to close and create hemodynamic problems, which may ultimately prove fatal unless treated.

One defect that may occur is a patent foramen ovale ("PFO") or patent ductus arteriosus ("PDA"), which may occur between the left and right atria of the heart. During fetal life, an opening called the foramen ovale allows blood to pass directly from the right atrium to the left atrium (bypassing the lungs). Thus, oxygenated blood from the placenta may travel through the vena cava into the right atrium, through the foramen ovale into the left atrium, and from there into the left ventricle for delivery via the aorta to the fetus' body. After birth, the foramen ovale is replaced with a membrane called the fossa ovalis, and over time, a solid mass of tissue may form.

Occasionally, this membrane and tissue mass fail to form or completely close the foramen ovale, which may be fatal if untreated. Similar defects may occur in other regions within a septum between chambers of the heart, such as atrial septal defects, ventricular septal defects, and the like.

To close such defects, open surgery may be performed to ligate and close the defect. Such procedures are obviously highly invasive and pose substantial morbidity and mortality risks.

Alternatively, catheter-based procedures have been suggested. These may involve introducing umbrella-like structures into the heart that include opposing expandable structures connected by a hub. One of the expandable structures is inserted through the defect, and both are expanded to secure the tissue surrounding the defect between the structures in an attempt to seal and close the defect. Such structures, however, involve frame structures that support membranes, both of which may fail during the life of the patient being treated, opening the defect, and/or releasing segments of the structure within the patient's heart.

Accordingly, apparatus and methods for closing patent foramen ovale, patent ductus arteriosus, or other septal defects would be considered useful.

SUMMARY OF THE INVENTION

The present invention is directed to apparatus and methods for closing patent foramen ovale ("PFO"), patent ductus arteriosus ("PDA"), or other septal defects.

In accordance with a first aspect of the present invention, an apparatus for closing a septal defect is provided that includes an elongate needle including a first end defining a tissue-penetrating tip, and a second end defining a substantially blunt tip. A filament extends from an intermediate portion of the needle between the first and second ends, and a locking element, such as a clip, clamp, cross-brace, and the like, may be securable to the filament, thereby preventing the locking element from moving along the filament away from the needle.

Preferably, the needle has a tapered cross-section such that the second end is substantially larger than the first end. A slot may be provided in the needle that extends from the intermediate portion to the second end, the slot having a size for receiving a portion of the filament therein. The second end of the needle may include a flared outer edge and/or a rounded inner edge.

In one embodiment, the locking element may be a clip that is slidable along the filament towards the needle, the clip including opposing arms having teeth or other engaging elements for preventing the clip from being moved along the filament away from the needle. Alternatively, the clip may be plastically deformable such that the clip may received around the filament and then crimped or otherwise secured to the filament during closure of a septal defect, as explained further below.

In accordance with another aspect of the present invention, a delivery apparatus for delivering a needle apparatus, such as that described above, is provided that includes an outer catheter and a pusher member that are slidably coupled to one another. The catheter may be a tubular member including proximal and distal ends and a lumen therebetween, the distal end having a size for insertion into a blood vessel or other body lumen. The needle may be carried within the lumen such that the first end is disposed distally to the second end.

The pusher member may be an inner catheter or other elongate member that is disposed within the lumen of the outer catheter. The pusher member may include a distal end that may be disposed proximate the second end of the needle, the pusher member being movable axially relative to the tubular member for ejecting the needle distally from the lumen. The pusher member may include a lumen extending proximally from the distal end of the pusher member such that the filament extending from the needle may be received through the lumen.

An actuator may be provided on the proximal end of the tubular member and/or the pusher member for advancing the pusher member relative to the tubular member. Preferably, the actuator may limit advancement of the pusher member such that the distal end of the pusher member extends only a predetermined distance beyond the distal end of the tubular member when activated. The actuator may also be coupled to the filament received through the lumen in the pusher member for applying proximal tension to the filament during use, as described further below.

The lumen of the catheter may include an enlarged distal region proximate the distal end for receiving the needle therein. For example, the second end of the needle may have a cross-section that is substantially larger than a cross-section of the distal end of the pusher member. In addition, the second end of the needle may have a flared outer edge such that the second end extends laterally from the distal end of the pusher member. Alternatively, the second end of the needle may simply be larger in cross-section than the distal end of the pusher member, In addition, the second end of the needle may include a rounded edge for facilitating pivoting of the needle about the intermediate region when the filament is pulled proximally.

In addition, the delivery apparatus may include a clip carrier having a proximal end and a distal end having a size for introduction into a body lumen. A clip or other locking element may be releasably carried by the distal end of the clip carrier, the clip including opposing arms defining a slot therebetween for receiving a filament therein. The clip carrier may include a hammer/anvil arrangement for plastically deforming at least one of the opposing arms to engage a filament received within the slot. The clip carrier may be completely separate from the catheter and pusher member or may be carried by the catheter and/or pusher member. For example, the catheter may include an additional lumen through which the clip carrier may be advanced.

In a further alternative, the delivery apparatus may include an imaging device including an imaging element associated with the distal end of the tubular member for imaging beyond the distal end of the tubular member. For example, the imaging device may be an endoscope or ultrasound device that may be received within a lumen of the tubular member or may be a separate device that may introduced independently into the patient but used in conjunction with the delivery apparatus during a procedure.

In accordance with yet another aspect of the present invention, a method is provided for closing a PFO or other septal defect within a patient's heart. Generally, the septal defect includes a flap of tissue partially detached from a septum wall between first and second chambers of the heart, the flap of tissue and surrounding tissue of the septum wall defining a septal opening through the septum wall. Initially, a needle may be provided that includes a first end defining a tissue-penetrating tip, a second end defining a substantially blunt tip, and an intermediate portion between the first and second ends from which a filament extends.

The needle may be advanced through the patient's vasculature until the needle is disposed within the first chamber of the heart adjacent the septal opening. For example, the needle may be disposed within a distal end of a delivery apparatus including a catheter and a pusher member slidably coupled to one another. The distal end of the delivery apparatus may be advanced through the patient's vasculature, e.g., from a percutaneous entry site, into the first chamber until the distal end is disposed adjacent the flap of tissue.

The first end of the needle may be directed through the flap of tissue until the second end passes through the flap of tissue and the needle is disposed within the second chamber of the heart. For example, the pusher member may be advanced distally relative to the catheter, thereby directing the needle from within the delivery apparatus and into and through the flap of tissue. Preferably, the pusher member is advanced a predetermined distance, e.g., such that the distal end of the pusher member extends completely through the flap of tissue to ensure that the needle is directed entirely into the second chamber.

The filament may then be pulled proximally, thereby causing the needle to pivot about the intermediate region such that the first and second ends of the needle straddle the septal opening within the second chamber. As the filament is pulled, the blunt tip of the needle may engage a distal surface of the flap of tissue, thereby preventing the needle from being pulled back through the flap of tissue. The blunt tip of the needle may include an enlarged or flared end, e.g., larger than the distal end of the pusher member, also to prevent the needle from being pulled through the flap of tissue. Instead, the blunt tip of the needle may slide along a distal surface of the flap of tissue and/or the septum wall, thereby causing the needle to pivot about the intermediate region of the needle. Preferably, the blunt tip of the needle includes a rounded inner edge for facilitating movement of the needle along the distal surface.

The flap of tissue may be directed into engagement with the septum wall to at least partially close the septal opening. For example, a locking element may be secured to the filament, the locking element engaging the proximal surface of the flap of tissue to secure the flap of tissue between the needle and the locking element. To accomplish this, a clip carrier may be introduced into the first chamber of the heart. The clip carrier may be manipulated to receive the filament within a clip carried by the clip carrier, and then the clip may be crimped or otherwise plastically deformed, e.g., by a mechanical crimper on the clip carrier, to secure the clip to the filament. Alternatively, a locking element may be slidably secured on the filament. The locking element may be slid along the filament towards the needle until the flap of tissue is secured against the tissue surrounding the septal opening. The locking element may include teeth or other elements that accommodate sliding the locking element along the filament towards the needle, but prevent subsequent movement of the locking element along the filament away from the needle. In addition, the needle and/or locking element may have lengths greater than a width of the septal opening, such that the flap of tissue may be secured between the needle and the locking element, thereby substantially closing the septal opening. The filament may be cut or otherwise detached from the delivery apparatus, and the delivery apparatus removed from the patient's body.

In accordance with still another aspect of the present invention, an apparatus is provided that includes an elongate needle including a first end defining a tissue-penetrating tip, a second end defining a substantially blunt tip, and a longitudinal axis extending between the first and second ends. A filament extends from an intermediate portion of the needle between the first and second ends. At least a segment of the filament may be biased towards a configuration defining a plane extending generally parallel to the longitudinal axis. Thus, the filament may be extendable towards a generally linear configuration, but may resiliently attempt to return towards the planar configuration.

In a preferred embodiment, the filament includes first and second segments. The first segment may be attached to the intermediate portion of the needle and biased to extend transversely with respect to the longitudinal axis. The second segment extends from the first segment and may be biased to extend transversely to the first segment such that the second segment defines the plane that extends generally parallel to the longitudinal axis of the needle. The second segment may be biased towards a coiled configuration, the coiled configuration lying substantially within the plane. Alternatively, the second segment may be biased towards other planar configurations lying substantially within the plane, for example, including at least one of an "L," a "U," a "Y," and/or an "S" shape.

The apparatus may include a tubular member, including proximal and distal ends and a lumen extending therebetween. The distal end may have a size for insertion into a blood vessel. Generally, the needle is carried within the lumen such that the first end is disposed distally to the second end. A pusher member may be slidably disposed within the lumen, the pusher member including a distal end disposed proximate the second end of the needle. Preferably, the pusher member is movable axially relative to the tubular member for ejecting the needle distally from the lumen.

The pusher member and/or the tubular member may include a gripping mechanism for releasably securing a loose end of the filament, thereby restraining the filament in the generally linear configuration. An actuator may also be provided on the proximal end of the pusher member and/or the tubular member for releasing the loose end of the filament, whereupon the filament may be free to assume the planar configuration.

The apparatus may be used for closing a septal defect within a patient's heart, similar to the embodiment described above. The needle may be advanced through the patient's vasculature, e.g., within the tubular member, until the needle is disposed within the first chamber of the heart adjacent the septal opening. The first end of the needle may be directed through the flap of tissue until the second end passes through the flap of tissue and the needle is disposed within the second chamber of the heart. The filament may be pulled, thereby causing the needle to pivot about the intermediate region such that the first and second ends of the needle straddle the septal opening within the second chamber. The filament may then be released, the filament resiliently assuming a generally planar configuration, thereby engaging the flap of tissue between the needle and the filament to at least partially close the septal opening.

Other objects and features of the present invention will become apparent from consideration of the following description taken in conjunction with the accompanying drawings.

BRIEF DESCRIPTION OF THE DRAWINGS

FIG. 1 is a perspective view of a first preferred embodiment of a needle apparatus for closing a septal defect, in accordance with the present invention.

FIG. 2 is a cross-sectional side view of a delivery apparatus for delivering the needle apparatus of FIG. 1.

FIG. 3 is a cross-sectional view of a heart including a PFO in a septum wall of the heart, showing an apparatus being introduced for treating the PFO.

FIGS. 4A and 4B are perspective details of the PFO of FIG. 3, showing a method for closing a PFO using the needle apparatus of FIG. 1.

FIGS. 5A–5D are cross-sectional views, showing a method for closing a PFO using the needle apparatus of FIG. 1.

FIG. 6 is a perspective view of a second preferred embodiment of a needle apparatus for closing a septal defect, in accordance with the present invention.

DETAILED DESCRIPTION OF THE PREFERRED EMBODIMENTS

Figure 7:
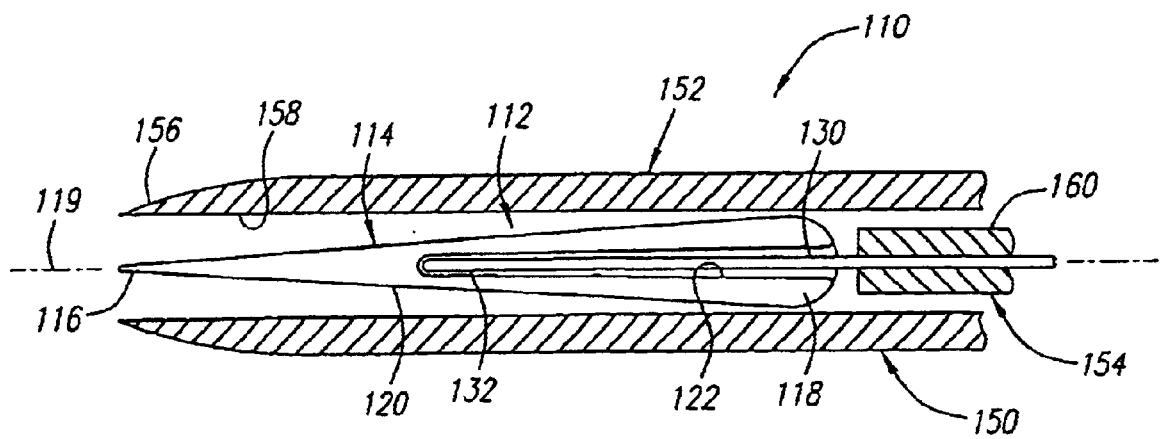
FIG. 7 is a cross-sectional side view of an apparatus for delivering the needle apparatus of FIG. 6.

Turning now to the drawings, FIGS. 1 and 2 show a first preferred embodiment of an apparatus 10 for closing a septal defect, such as a PFO or PDA, in accordance with the present invention. Generally, the apparatus 10 includes a needle apparatus 12 and a delivery apparatus 50 for introducing and deploying the needle apparatus 12.

With particular reference to FIG. 1, the needle apparatus 12 includes an elongate needle 14 including a first end 16 defining a tissue-penetrating tip, a second end 18 defining a substantially blunt tip, and an intermediate region 20 between the first and second ends 16, 18. The needle 14 may be formed from a variety of substantially rigid biocompatible materials, e.g., stainless steel.

Preferably, the needle 14 includes a longitudinal slot 22 therein that extends between the intermediate region 20 and the second end 18. The second end 18 of the needle 14 may include a flared outer edge 24 that extends transversely outwardly, and a rounded inner edge 26. The second end 18 of the needle 14 preferably has a cross-section that is substantially larger than the first end 16, and more preferably that is substantially larger than the intermediate region 20. For example, the second end 18 may have a generally "U" shape, as shown, defining the slot 22 therein.

The needle apparatus 12 also includes a filament 30 that extends from the intermediate region 20 of the needle 14. The filament 30 is preferably formed from a substantially inelastic biocompatible material, such as non-bioabsorbable suture material, e.g., plastic. Preferably, a first end 32 of the filament 30 is substantially permanently attached to the intermediate region 20, e.g., through a loop 34 on the intermediate region 20, and a second end (not shown) of the filament 30 is loose. Alternatively, a wall of the intermediate region 20 may include a hole (not shown) through which the first end 32 of the filament 30 may be secured. In a further alternative, the intermediate region 20 may include a recess, groove, slot, and the like (not shown), for receiving the first end 32, e.g., such that the filament 30 may be tied around the intermediate region 20 and received within the recess. In addition or alternatively, the first end 32 of the filament 30 may be attached to the needle 14 by an adhesive or other bonding method, sonic welding, and the like.

In addition, the needle apparatus 12 may also include a clip or other locking element 40 that may be secured to the filament 30. In a preferred embodiment, the clip 40 includes opposing arms 42 defining a slot 44 therebetween for receiving the filament 30 therein. The inner surfaces of the arms 42 may include teeth or other engaging elements (not shown) that allow the clip 40 to be directed along the filament 30 towards the needle 12, but prevent the clip 40 from being moved along the filament 30 away from the needle 12. Alternatively, the clip 40 may be plastically deformable such that the arms 42 may be disposed initially apart sufficient to freely introduce the filament 30 therebetween, and then crimped or otherwise directed towards one another to frictionally secure the clip 40 at a desired location on the filament 30.

With particular reference to FIG. 2, the delivery apparatus 50 generally includes an outer catheter or tubular member 52, and an inner catheter or pusher member 54. The outer catheter 52 includes a proximal end (not shown), and a distal end 56 having a size for insertion into a blood vessel or other body lumen (not shown). The distal end 56 preferably has a tapered and/or rounded distal tip 58, e.g., for facilitating substantial atraumatic advancement of the delivery apparatus 50 through a patient's vasculature. The outer catheter 52 also includes a lumen 60 therein that extends between the proximal and distal ends 56. In the embodiment shown, the lumen 60 includes an enlarged distal region 62 having a size for receiving the needle 12. Preferably, the needle 14 may be received in the enlarged distal region 62 such that the first end 16 is disposed distally to the second end 18 therein.

The pusher member 54 includes a proximal end (not shown) and a distal end 64 having a size such that the pusher member 54 may be slidably disposed within the lumen 60 of the outer catheter 52. The distal end 64 is preferably substantially blunt and has a cross-section that is substantially smaller than a projected cross-section of the needle 12. The distal end 64 is disposed proximate the second end 18 of the needle 12, and the pusher member 54 is movable axially relative to the outer catheter 52 for ejecting the needle 12 distally from the lumen 60, as described further below. In a preferred embodiment, the pusher member 54 includes a lumen 66 extending proximally from the distal end 64 of the pusher member 54, and preferably extending to the proximal end of the pusher member 54 As shown, the lumen 66 has a size for receiving the filament 30 therethrough.

Alternatively, the pusher member 54 may include a longitudinal groove or slot (not shown) extending along an outer wall of the pusher member 54 from the distal end 64 to the proximal end. The groove or slot may have a size for slidably receiving the filament 30 therein. In a further alternative, the delivery apparatus may include interlocked rails (not shown) that may slide axially relative to one another in a controlled manner, instead of the outer catheter 52 and the pusher member 54.

An actuator, e.g., a handle device (not shown), may be provided on the proximal end of the outer catheter 52 and/or the pusher member 54 that may limit relative axial movement of the outer catheter 52, the pusher member 54, and/or the filament 30. For example, the actuator may be fixed to the outer catheter 52 and coupled to the pusher member 54 for advancing the pusher member 54 relative to the outer catheter 52 (or alternatively, for retracting the outer catheter 52 relative to the pusher member 54). Preferably, the actuator allows advancement of the pusher member 54 such that the distal end 64 of the pusher member 54 extends a predetermined distance beyond the distal tip 58 of the outer catheter 52 and then prevents further distal advancement. In addition, the actuator may be coupled to the second end of the filament 30, e.g., for pulling the filament proximally relative to the outer catheter 52 and/or pusher member 54, as described further below.

Use of the apparatus 10 for closing a septal defect 94 is shown in conjunction with FIGS. 3–5D. FIG. 3 generally shows a heart 90 of a patient, including heart chambers 91, 92 separated by a septum wall 93. The septal defect 94, such as a PFO or PDA, is shown in the septum wall 93, which may be located in the septum wall between the right atrium and the left atrium of the heart. As best seen in FIGS. 4A–5D, the septal defect 94 may include a flap of tissue 95 that is at least partially detached from the septum wall 93, thereby defining an opening 96 in the septum wall 93. Alternatively, the septal defect may be an opening that extends through the septum wall 93, e.g., laterally such that the septal defect includes flaps of tissue that partially overlap one another (not shown).

The apparatus 10, i.e., the delivery apparatus 50 with the needle apparatus 12 therein (the latter not shown in FIG. 3, see FIGS. 5A–5D), may be introduced into the patient's vasculature, e.g., from a percutaneous entry site in a peripheral vessel, such as the femoral artery, carotid artery, and the like (not shown). The apparatus 10 may be advanced endoluminally within the patient's vasculature, e.g., through the aortic arch 97 and into the heart 90 until the distal end 56 is disposed within the chamber 91, which is shown in FIG. 3 to be the left atrium. Preferably, access into the heart 90 may be obtained using a venous approach. The apparatus 10 may be introduced percutaneously into a peripheral vein, such as the femoral or jugular vein, and advanced through the vena cava (not shown) into the right atrium.

With particular reference to FIGS. 5A–5D, the distal end 56 of the apparatus 10 may be advanced into contact with a proximal surface 95a of the flap of tissue 95, e.g., such that the flap of tissue 95 is disposed proximate the septal opening 96, as shown in FIG. 5A (e.g., within the right atrium, not shown). The pusher member 54 may be advanced distally relative to the outer catheter 52, thereby piercing the first end 16 of the needle 14 through the flap of tissue 95 until the needle 14 enters the chamber 92 beyond the septum wall 93 (e.g., the left atrium, not shown), thereby creating a puncture 99. Preferably, the penetrating tip on the first end 16 of the needle 14 is substantially sharp to facilitate piercing and passing through the flap of tissue 95. The substantially blunt tip on the second end 18 of the needle 14 enhances engagement with the distal end 64 of the pusher member 54 to facilitate pushing the needle 14 through the flap of tissue 95 to create the puncture 99.

Preferably, the pusher member 54 is advanced distally until the second end 18 of the needle 14 passes entirely through the flap of tissue 95, as shown in FIG. 5B. For example, the actuator (not shown) on the delivery apparatus 50 may allow controlled advancement of the pusher member 54 to allow the distal end 64 of pusher member 54 to be disposed a predetermined distance beyond the distal tip 58 of the outer catheter 52. Preferably, the predetermined distance is a distance greater than a thickness of the flap of tissue 95, e.g., at least about two to ten millimeters (2–10 mm), such that the distal end 64 of the pusher member 54 passes through the puncture 99, thereby ensuring that the second end 18 of the needle 14 is advanced completely beyond the distal surface 95b of the flap of tissue 95.

The pusher member 54 may then be retracted proximally, e.g., to withdraw the distal end 58 back through the flap of tissue 95 and at least partially into the lumen 60 of the outer catheter 52. The filament 30 may be pulled proximally, either before or after retraction of the pusher member 54, thereby causing the second end 18 of the needle 14 to engage the distal surface 95b of the flap of tissue 95. Because of the substantially blunt tip on the second end 18, the needle 14 may not pass back through the puncture. Preferably, because of the flared outer edge 24, the second end 18 of the needle 14 is offset laterally relative to the distal end 64 of the pusher member 54, thereby preventing the second end 18 from following the pusher member 54 back through the puncture 99. Thus, the second end 18 engages the distal surface 95b and retains the needle 14 entirely within the chamber 92.

With particular reference to FIG. 5C, because the filament 30 is coupled to the intermediate region 20 of the needle 14, continued pulling of the filament 30 proximally may cause the needle 14 to pivot about the intermediate region 20. Preferably, the rounded inner edge 26 allows the second end 18 of the needle 14 to slide and pivot along the distal surface 95b of the flap of tissue 95 and/or along the septum wall 93. As the filament 30 is pulled further, the needle 14 is directly substantially transversely, and preferably substantially parallel to the septum wall 93, e.g., until it abuts the distal surface 95b of the flap of tissue 95 and/or the septum wall 93, as best seen in FIGS. 4A and 5C. Preferably, a length of the needle 14 is substantially longer than a width of the opening 96 such that the first and second ends 16, 18 of the needle 14 straddle the opening 96 and engage the septum wall 93 on either side of the septal defect 94.

As best seen in FIGS. 4B and 5D, the clip 40 may then be secured to the filament 30 such that the clip 40 substantially abuts the proximal surface 95a of the flap of tissue 95. For example, in one embodiment, the clip 40 may be provided within the lumen of the outer catheter 54 and advanced along the filament 30 towards the needle 14 until the clip 54 contacts the proximal surface 95a. As the clip 40 is directed further distally, the flap of tissue 95 is forced into contact with the septum wall 93 surrounding the opening 96, possible even filling the opening 96, as shown in FIG. 4B.

Alternatively, the clip 40 may be carried by a separate device (not shown) than the delivery apparatus 50. For example, a clip carrier (not shown) may be introduced into the chamber 91, e.g., from a percutaneous entry site (not shown), and advanced endoluminally into the chamber 92. In a further alternative, the outer catheter 52 of the delivery apparatus 50 may include an additional lumen (not shown) from which a clip carrier may be advanced.

The clip 40 may be directed around the filament 30 and secured within the slot of the filament 30. For example, the clip carrier may include a hammer-anvil arrangement (not shown) that may be used to crimp or otherwise plastically deform the clip 40 to substantially engage the filament 30. Preferably, tension is applied to the filament 30, and the clip 40 is brought into close proximity with the proximal surface 95a of the flap of tissue 95 before the clip 40 is crimped, thereby securing the clip 40 against the flap of tissue 95.

Alternatively, the clip 40 may be slidably received on the filament 30, e.g., by a separate clip carrier (not shown) or may be provided on the filament 30 within the delivery apparatus 50 (also not shown). One or more tools may be used to apply proximal tension to the filament 30 and drive the clip 40 distally towards the needle 14, e.g., until the clip 40 engages the flap of tissue 95.

This arrangement of needle apparatus 12 may be used for a flap of tissue 95 that falls proximally away from the opening 96 in the septum wall 93 (into the proximal chamber 91 shown in FIG. 3). As the clip 40 is advanced distally over the filament 30, the first and second ends 16, 18 of the needle 14 may provide anchors such that the clip 40 may push the flap of tissue 95 into the opening 96 and/or into contact with the surrounding septum wall 93.

Alternatively, if the flap of tissue 95 falls distally away from the opening 96 (not shown), the filament 30 may be pulled proximally in order to cause the needle 14 to direct the flap of tissue 95 into contact with the septum wall 93 surrounding the opening 96 and/or to substantially fill the opening 96. To hold the flap of tissue 95 in this closed position, a clip (not shown) may be advanced over the filament 30 or otherwise secured to the filament 30. Preferably, the clip has a length or cross-section that is greater than the cross-section of the opening 96 such that the clip abuts the septum wall 93 surrounding the opening 96. Thus, the flap of tissue 95 may be sandwiched between the needle 14 and the clip, which engage opposing surfaces of the surrounding septum wall in order to secure the flap of tissue 95 substantially closed.

Once the needle 14, clip 40, and flap of tissue 95 are secured as desired, the filament 30 may be cut and the delivery apparatus 50 removed from the patient's body. For example, the clip carrier may include a cutting element (not shown) that may be used to cut the filament at a location close to the clip 40, as shown in FIGS. 4B and 5D. The cutting element may simply be a blade, scissors, and the like that is deployable from the clip carrier. Alternatively, a cutting element may be advanced through a lumen (not shown) in the outer catheter 52, or may be a separate device that may be introduced independently through the patient's vasculature into the chamber 92 of the heart 90.

It will be appreciate by those skilled in the art that the procedure described herein may be monitored in a variety of ways. For example, the delivery apparatus 50 may include an imaging device, such as an endoscope or other fiber optic device, an intravascular ultrasound ("IVUS") device, and the like (not shown). The device may be provided on the distal end 56 of the outer catheter 52, e.g., attached to or adjacent the distal tip 58 or advanceable from a lumen (not shown) therein. In a further alternative, external imaging may be used, either alone or in conjunction with direct visualization. For example, the needle 14, the clip 40, the outer catheter 52, and/or the pusher member 54 may include radiopaque markers (not shown) at predetermined locations that may be observed using fluoroscopy and the like.

Turning to FIGS. 6 and 7, another preferred embodiment of an apparatus 110 is shown for closing a septal defect, such as a PFO or PDA, that generally includes a needle apparatus 112 and a delivery apparatus 150 for introducing and deploying the needle apparatus 112.

With particular reference to FIG. 6, the needle apparatus 112 includes an elongate needle 114 including a first end 116 defining a tissue-penetrating tip, a second end 118 defining a substantially blunt or rounded tip, and a longitudinal axis 119 between the first and second ends 116, 118. The needle 114 may be formed from a variety of substantially rigid biocompatible materials, e.g., stainless steel.

Preferably, the needle 114 includes a longitudinal slot 122 therein that extends between an intermediate region 120 of the needle 114 and the second end 118. The second end 118 of the needle 114 may include a flared outer edge and/or a rounded inner edge (not shown), similar to the previous embodiment. The second end 118 of the needle 114 preferably has a cross-section that is substantially larger than the first end 116, and more preferably that is substantially larger than the intermediate region 120. For example, the second end 118 may have a generally "U" shape, as shown, defining the slot 122 between edges 123.

The needle apparatus 112 also includes a filament 130 that extends from the intermediate region 120 of the needle 114. The filament 130 may be formed from a superelastic and/or shape memory material, such as Nitinol. Preferably, the filament 130 is biased towards a coiled configuration, such as that shown in FIG. 6, yet may be deformed into a generally linear configuration, such as that shown in FIG. 7. A first end 132 of the filament 130 is substantially permanently attached to the intermediate region 120, e.g., by bonding or welding, similar to the previous embodiment. Preferably, the first end 132 is attached within or adjacent to the slot 122, and a second end 133 of the filament 130 is loose.

In its unstressed or relaxed state, the filament 130 includes a first segment 134 that extends from the first end 132 transversely, and preferably substantially perpendicularly, to the longitudinal axis 119. The filament 130 also includes a second segment 136 that extends transversely from the first segment 134, and preferably substantially perpendicularly to the first segment 134. More preferably, the second segment 136 is biased to define a planar configuration, e.g., in the shape of a coil, as shown in FIG. 6. The planar configuration generally defines a plane that extends substantially parallel to the longitudinal axis 119 of the needle 114.

Alternatively, the second segment 136 may be biased towards other configurations instead of a coil that generally define a plane. For example, at least a portion of the second segment 136 may be biased towards a generally "L," "U," "Y," and/or "S" shape lying within the plane.

Turning to FIG. 7, the delivery apparatus 150 generally includes a sheath or outer member 152, and an inner pusher member 154. The sheath 152 generally is an elongate tubular member including a proximal end (not shown), a distal end 156, and a lumen 158 extending therebetween. The distal end 156 preferably has a size and shape for facilitating insertion into and along a blood vessel or other body lumen (not shown). The lumen 158 has a size for receiving the needle 114 therein, preferably such that the first end 116 is disposed distally to the second end 118, as shown.

The pusher member 154 is slidably disposed within the lumen 158, and includes a distal end 160 that is disposed proximate the second end 118 of the needle 114. The pusher member 154 may be movable axially relative to the sheath 152 for ejecting the needle 114 distally from the lumen 158. The pusher member 154 includes a gripping mechanism (not shown) for releasably securing the loose end (also not shown in FIG. 7) of the filament 130. The gripping mechanism may retrain the filament 130 in the generally linear configuration, as shown in FIG. 7. The gripping mechanism may include a clamp (not shown) that may be slidably received in or otherwise coupled to the pusher member 154. The clamp may be opened to receive the loose end of the filament, closed to secure the filament thereto, and then opened again to release the filament, as explained further below. Alternatively, the filament may be directed into a slot (not shown) in the pusher member and secured within the slot by a coaxial member (also not shown) disposed within or around the pusher member 154.

An actuator (not shown) may be provided on the proximal end of the pusher member 154 and/or the sheath 152 for controlling or activating movement of the pusher member 154 relative to the sheath 152. In addition or alternatively, the actuator may be activated for releasing the loose end of the filament 130.

In addition, an imaging element, such as an IVUS (not shown), may be associated with the distal end 156 of the tubular member 152 for imaging beyond the distal end 156 of the tubular member 152 during a procedure, similar to the previous embodiment.

Figure 8A:
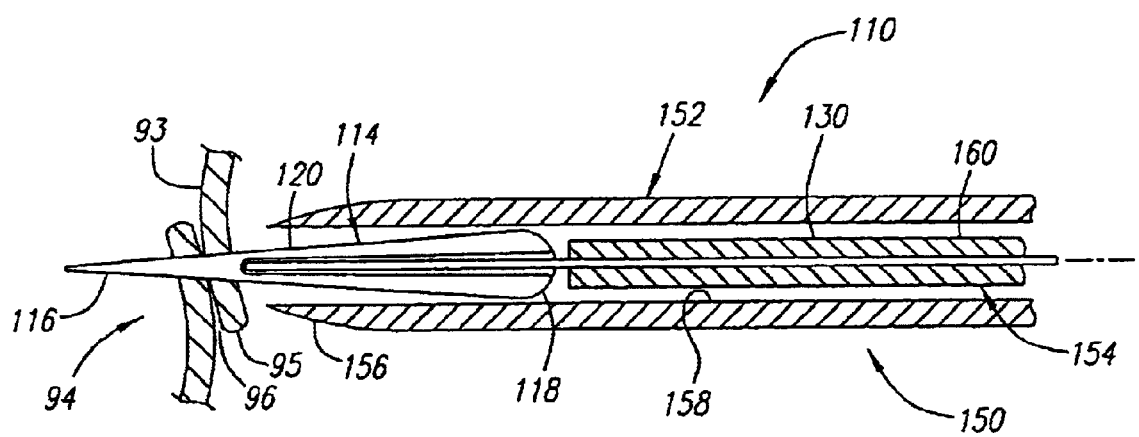
FIGS. 8A and 8B are cross-sectional views, showing a method for closing a PFO using the needle apparatus of FIG. 6.
Figure 8B:
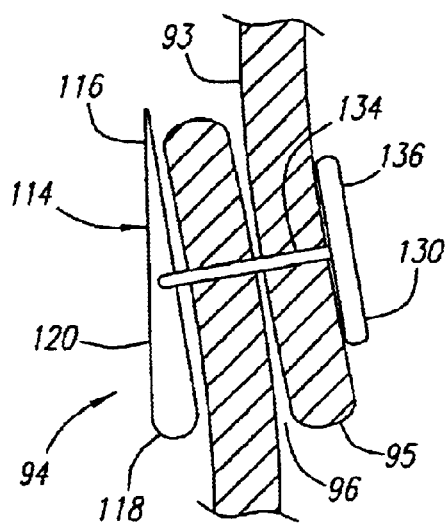

Turning to FIGS. 8A and 8B, the apparatus 110 may be used to close and/or seal a septal defect 94 within a patient's heart (not shown). Generally, the septal defect 94 includes a flap of tissue 95 partially detached from a septum wall 93 between first and second chambers of the heart, such as a PFO or PDA as described above, such that the flap of tissue 95 and surrounding tissue define a septal opening 96 through the septum wall 93.

Initially, a needle 114 may be provided that includes a first end 116 defining a tissue-penetrating tip, a second end 118 defining a substantially blunt tip, and an intermediate portion 120 between the first and second ends 116, 118 from which a filament 130 extends. The needle 114 may be disposed within a lumen 158 or otherwise carried by a sheath 152. Preferably, the filament 130 is secured to a pusher member 154, the distal end 160 of which is disposed adjacent the second end 118 of the needle 114.

The needle 114, e.g., within the sheath 152, may be advanced through the patient's vasculature until the needle 114 is disposed within the first chamber of the heart, e.g., adjacent the septal opening 96. The first end 116 of the needle 114 may be inserted through the flap of tissue 95, as shown in FIG. 8A, until the second end 118 passes through the flap of tissue 95 and an overlapping portion of the septum wall 93. Preferably, the pusher member 154 is advanced against the second end 118 of the needle, thereby directing the needle 114 entirely through the septum wall 93 until the needle 114 is disposed within the second chamber of the heart.

The filament 130 may then be pulled proximally, thereby causing the needle 114 to pivot about the intermediate region 120 such that the needle 114 extends substantially parallel to the septum wall 93. The first and second ends 116, 118 of the needle 114 may straddle the septal opening 95 within the second chamber, similar to the previous embodiment, or otherwise draw the flap of tissue 95 against the septum wall 93. The filament 130 may then be released from the pusher member 154, and the sheath 152 and pusher member 152 removed from the patient.

Once the second end of the filament 114 is released, because of its inherent bias, the filament 130 may resiliently assume a generally planar configuration, thereby engaging the flap of tissue 95 and/or the septum wall 93 between the needle 114 and the filament 130. Preferably, a first segment 134 of the filament 130 extends transversely from the needle 114, i.e., through the flap of tissue 95 and septum wall 95. A second segment 136 of the filament 130 assumes a planar configuration against the flap of tissue 95 to at least partially close the septal opening 95, as shown in FIG. 8B.

Preferably, as explained above, the filament 130 may assume a coiled configuration defining a plane that is generally parallel with the septum wall 93. The filament 130 in the coiled configuration may have sufficient width to engaging tissue surrounding the opening 96. Alternatively, the filament 130 may simply retain the needle 114 against the flap of tissue 95, thereby maintaining the flap of tissue 95 against the septum wall 93 to substantially close and/or seal the opening 96.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method for closing a septal defect within a patient's heart, the septal defect comprising a flap of tissue partially detached from a septum wall between first and second chambers of the heart, the flap of tissue and surrounding tissue defining a septal opening through the septum wall, the method comprising:

provTding a needle comprising a first end defining a tissue-penetrating tip, a second end defining a substantially blunt tip, and an intermediate portion between the first and second ends from which a filament extends;

advancing the needle through the patient's vasculature until the needle is disposed within the first chamber of the heart adjacent the septal opening;

directing the first end of the needle through the flap of tissue until the second end passes through the flap of tissue and the needle is disposed within the second chamber of the heart;

pulling the filament, thereby causing the needle to pivot about the intermediate region such that the first and second ends of the needle straddle the septal opening within the second chamber; and directing the flap of tissue into engagement with the septum wall to at least partially close the septal opening.

2. The method of claim 1, wherein the step of directing the flap of tissue comprises securing a locking element to the filament, the locking element engaging the proximal surface of the flap of tissue to secure the flap of tissue between the needle and the locking element.

3. The method of claim 2, wherein the step of securing the locking element comprises introducing a carrier member into the first chamber of the heart, the carrier member carrying the locking element.

4. The method of claim 2, wherein the carrier member is manipulated to receive the filament within a slot in the locking element, and wherein the locking element is crimped to secure the filament within the slot.

5. The method of claim 1, wherein a locking element comprises a clip slidably secured on the filament.

6. The method of claim 1, wherein the step of directing the flap of tissue comprises advancing the clip along the filament towards the needle until the flap of tissue is secured against the tissue surrounding the septal opening.

7. The method of claim 1, wherein the step of pulling the filament comprises slidably engaging the blunt tip of the needle along a distal surface of the flap of tissue, thereby causing the needle to pivot about the intermediate region of the needle.

8. The method of claim 7 edge for facilitating movement of the needle along the distal surface.

9. The method of claim 1, wherein the needle is disposed within a distal end of a delivery apparatus comprising a catheter and a pusher member slidably coupled to one another, and wherein the step of advancing the needle comprises advancing the distal end of the delivery apparatus into the first chamber until the distal end is disposed adjacent the flap of tissue.

10. The method of claim 9, wherein the step of directing the first end of the needle through the flap of tissue comprises advancing the pusher member distally relative to the catheter, thereby directing the needle from within the delivery apparatus.

11. A method for closing a septal defect within a patient's heart, the septal defect comprising a flap of tissue partially detached from a septum wall between first and second chambers of the heart, the flap of tissue and surrounding tissue defining a septala opening through the septum wall, the method comprising:

providing a needle comprising a first end defining a tissue-penetrating tip, a second end defining a substantially blunt tip, and an intermediate portion between the first and second ends from which a filament extends;

advancing the needle through the patient's vasculature until the needle is disposed within the first chamber of the heart adjacent the septal opening;

directing the first end of the needle through the flap of tissue until the second end passes through the flap of tissue and the needle is disposed within the second chamber of the heart;

pulling the filament, thereby causing the needle to pivot about the intermediate region such that the first and second ends of the needle straddle the septal opening within the second chamber; and releasing the filament, the filament resiliently assuming a generally planar configuration, thereby engaging the flap of tissue between the needle and the filament to at leaast partially close the septal opening.

* * * * *